(12) United States Patent
Seo et al.

(10) Patent No.: US 10,071,015 B2
(45) Date of Patent: Sep. 11, 2018

(54) WEARABLE DEVICE FOR IMPROVING TACTILE SENSITIVITY

(71) Applicant: UWM Research Foundation, Inc., Milwaukee, WI (US)

(72) Inventors: Na Jin Seo, Glendale, WI (US); Leah R. Enders, Milwaukee, WI (US)

(73) Assignee: UWM Research Foundation, Inc., Milwaukee, WI (US)

( * ) Notice: Subject to any disclaimer, the term of this patent is extended or adjusted under 35 U.S.C. 154(b) by 583 days.

(21) Appl. No.: 14/256,156

(22) Filed: Apr. 18, 2014

(65) Prior Publication Data

US 2014/0316309 A1    Oct. 23, 2014

Related U.S. Application Data (60) Provisional application No. 61/813,519, filed on Apr. 18, 2013.

(51) Int. Cl.
*A61H 23/00* (2006.01)
*A61H 23/02* (2006.01)
(Continued)

(52) U.S. Cl.
CPC ........... *A61H 23/02* (2013.01); *A61B 5/4827* (2013.01); *A61B 5/7475* (2013.01); *A61H 23/0218* (2013.01); *A61H 23/0263* (2013.01); *A61M 21/00* (2013.01); *A61H 2201/165* (2013.01); *A61H 2201/1635* (2013.01); (Continued)

(58) Field of Classification Search
CPC ............... A61H 23/02; A61H 23/0218; A61H 23/0263; A61H 2205/06; A61M 21/00; A61M 2205/8206; A61M 2021/0027; A61M 2209/088; A61M 2230/63; A61M 2205/502; A61M 2021/0022; A61B 5/7475; A61B 5/4827
See application file for complete search history.

(56) References Cited

U.S. PATENT DOCUMENTS 5,782,873 A   7/1998 Collins
6,032,074 A   2/2000 Collins
(Continued)

OTHER PUBLICATIONS

Collins, J.J. et al., "Noise-enhanced tactile sensation," Nature, vol. 383, pp. 770 (1996).
(Continued)

*Primary Examiner* — Quang D Thanh
(74) *Attorney, Agent, or Firm* — Michael Best & Friedrich LLP (57) ABSTRACT

A method increases a tactile sensitivity of a fingertip of a user with a wearable device. The wearable device includes a vibrating element, an actuator for receiving user input, and a control circuitry. The method includes positioning the vibrating element on one of a user's arm, wrist, hand, or proximal finger segment and activating the vibrating element to apply a vibrating force at a first magnitude. The method also includes receiving user input indicating that the user detected movement of the vibrating element at the first magnitude and applying the vibrating force at a second magnitude, the second magnitude being lower than the first magnitude, to increase the tactile sensitivity of at least one fingertip of the user.

21 Claims, 8 Drawing Sheets

(51) Int. Cl.
A61B 5/00 (2006.01)
A61M 21/00 (2006.01)
(52) U.S. Cl.
CPC .............. A61H 2201/5005 (2013.01); A61H 2201/5043 (2013.01); A61H 2205/06 (2013.01); A61H 2205/065 (2013.01); A61H 2205/067 (2013.01); A61M 2021/0022 (2013.01); A61M 2021/0027 (2013.01); A61M 2205/502 (2013.01); A61M 2205/8206 (2013.01); A61M 2209/088 (2013.01); A61M 2230/63 (2013.01)

(56) References Cited

U.S. PATENT DOCUMENTS

| | | | |
|---|---|---|---|
| 7,349,739 | B2 | 3/2008 | Harry et al. |
| 8,040,223 | B2 | 10/2011 | Mortimer et al. |
| 8,308,665 | B2 | 11/2012 | Harry et al. |
| 8,369,955 | B2 | 2/2013 | Faubert et al. |
| 8,958,886 | B2 | 2/2015 | Schepis et al. |
| 8,974,402 | B2 | 3/2015 | Oddsson et al. |
| 9,011,355 | B2 | 4/2015 | Ehrenreich et al. |
| 9,072,896 | B2 | 7/2015 | Dar et al. |
| 9,095,417 | B2 | 8/2015 | Dar et al. |
| 2006/0020452 | A1 | 1/2006 | Nakatani et al. |
| 2007/0100262 | A1* | 5/2007 | Simos ............... A61H 23/02 601/74 |
| 2008/0027363 | A1* | 1/2008 | Brueckmann ...... A61H 23/0263 601/70 |
| 2008/0077192 | A1 | 3/2008 | Harry et al. |
| 2009/0023122 | A1* | 1/2009 | Lieberman ........... G09B 19/003 434/258 |
| 2011/0005532 | A1 | 1/2011 | Faubert et al. |
| 2011/0251520 | A1 | 10/2011 | Shieh et al. |
| 2012/0259255 | A1 | 10/2012 | Tomlinson et al. |
| 2013/0041296 | A1 | 2/2013 | Tass et al. |
| 2014/0309709 | A1 | 10/2014 | Gozani et al. |
| 2015/0105840 | A1 | 4/2015 | Boggs, II |
| 2015/0151124 | A1 | 6/2015 | Mueller et al. |
| 2015/0164737 | A1 | 6/2015 | Ludlow et al. |
| 2015/0174391 | A1 | 6/2015 | Wistrand et al. |

OTHER PUBLICATIONS

Dinse, H.R. et al., "Tactile coactivation resets age-related decline of human discrimination," Annals of Neurology, vol. 60, pp. 88-94 (2006).
Kitajo, K. et al., "Behavioral stochastic resonance within the human brain," Phys. Rev. Lett., vol. 90 (2003).
Kitajo, K. et al., "Noise-induced large-scale phase synchronization of human-brain activity associated with behavioural stochastic resonance," Europhysics Letters, vol. 80 (2007).
Lugo, E. et al., "Ubiquitous crossmodal Stochastic Resonance in Humans: auditory noise Facilitates tactile, visual and proprioceptive sensations," PLoS One, vol. 3 (2008).
Mori, T. et al., "Noise-induced entrainment and stochastic resonance in human brain waves," Phys.. Rev. Lett., vol. 88 (2002).
Ward, L.M., "Physics of neural synchronisation mediated by stochasitic resonance," Contemporary Physics, vol. 50, pp. 563-574 (2009).
Ward, L.M. et al., "Stochasitc resonance modulates neural synchronization within and between cortical sources," PLoS One, vol. 5 (2010).
Alawieh, N., "Tactor to Optimize Skin Response to Vibration," pp. 1 (2011).
Augurelle, AS et al., "Importance of Cutaneous Feedback in Maintaining a Secure Grip During Manipulation of Hand-Held Objects," 89, pp. 665-671 (2003).
Bell-Krotoski, J., "Testing Sensibility, Including Touch Pressure, Two-Point Discrimination," Point Localization and Vibration, pp. 77-86 (1993).
Bhakta, BB et al., "Use of Botulinum Toxin in Stroke Patients with Severe Upper Limb Spasticity," J Neural Neurosurg Psychiatry, 61, pp. 30-35 (1996).
Bjorkman, A et al "Acute Improvement of Hand Sensibility After Selective Ipsilateral Cutaneos Forearm Anaesthesia," 20, pp. 2733-2736 (2004).
Blennerhassett, JM et al., "Grip Force Regulation During Pinch Grip Lifts Under Somatosensory Guidance: Comparison Between People with Stoke and Healthy Controls," 87, pp. 18-429 (2006).
Box, Gep., "An Analysis of Transformations," Journal of the Royal Statistical Society, 26, pp. 211-252 (1964).
Briggs, R.W et al "A Pneumatic Vibrotactile Stimulation Device for fMRI," Magnetic Resonance, 51, pp. 640-643 (2004).
Bureau of Labor Statistics, Census of Fatal Occupational Injuries, (2009).
Bureau of Labor Statistics, Survey of Occupational Injuries and Illnesses, (1993).
Byl, N et al., "Effectiveness of Sensory and Motor Rehabilitation of the Upper Limb Following the Principles of Neuroplasticity: Patients Stable Post stroke" Neurorehabil Neural Repair 84, pp. 428-442 (2005).
Carey et al., "Frequency of Discriminative Sensory Loss in the Hand After Stoke in a Rehabilitation Setting," J. Rehabil Med, 43, pp. 257-263 (2011).
Carey, LM et al., "Training of Somatosensory Discrimination After Stroke: Facilitation of Stimulus Generalization," AM J Phys Med Rehabil, 84, pp. 428-442 (2005).
Carey., "Somatosensory Loss After Stroke," Critical Reviews in Physical and Rehabilitation Medicine, 7, pp. 51-91 (1995).
Collins, JJ et al., Noise-Mediated Enhancements and Decrements in Human Tactile Sensation, 56, pp. 923-926 (1997).
Conrad, MO et al., "Effects of Wrist Tendon Vibration on Targeted Upper Arm Movements in Post stroke Hemiparesis," Neurorehabil Neural Repair, 25, pp. 61-70 (2011).
Craig, JC et al., "The Two Point Threshold: Not a Measure of Tactile Spatial Resolution Current Directions in Psychological Science," 9, pp. 29-32 (2000).
Digikey., "Piezoelectric Vibrators" (2011).
Enders, L et al., "Remote Vibrotactile Noise Improves Light Touch Sensation in Stroke Survivors' Fingertip's via Stochastic Resonance," Journal of NeuroEngineering and Rehabilitation, pp. 1-8 (2013).
Engineering Acoustics, Inc., "C-3 Tactor," pp. 1 (2014).
Fell, J et al., "The Role of Phase Synchronization in Memory Processes," Nature Reviews, 12, pp. 105-118 (2011).
Fugl-Meyer et al., "The Post-Stroke Hemiplegic Patient, 1. A Method for Evaluation of Physical Performance," Scand J Rehabil Med, 7, pp. 13-31 (1975).
Galica, AM et al., "Subsensory Vibration to the Feet Reduce Gait Variablility in Elderly Falters," Gait Posture, 30, pp. 383-387 (2009).
Gray et al., "Motor Recovery Following Acute Stroke" Age and Ageing, 19, pp. 179-184 (1990).
Harrington, W et al., "A New Vibrotactile Stimulator for Functional MRI," Neuromagnetic Research Laboratory, 10, pp. 140-145 (2000).
Hur, P et al., "Investigating the Role of Vibrotactile Noise in Early Response to Perturbation," (2014).
Johansson, RS et al "Roles of glabrous Skin Receptors and Sensorimotor Memory in Automatic Control of Precision Grip When Lifting Rougher or More Slippery Objects," 56, pp. 550-564 (1984).
Kim et al., "Discriminative Sensory Dysfunction After Unilateral Stroke," 27, pp. 677-682 (1996).
Kou, W et al., "Vibrotactile Device for Optimizing Skin Response to Vibration," Department of Biomedical Engineering, pp. 1-6 (2012).
Kurita, Y et al., "Sensorimotor Enhancer for a Fingertip Based on Stochastic Resonance," International Conference on Robotics and Automation, pp. 3790-3795 (2011).
Kurita, Y et al., "Wearable Sensorimotor Enhancer for Fingertip Based on Stochastic Resonance Effect," 43. pp. 333-337 (2013).
Liberty Mutual, Workplace safety index, (2010).

(56) References Cited

OTHER PUBLICATIONS

Liu, W et al., "Noise-Enhanced Vibrotactile Sensitivity in Older Adults, Patients with Stroke, and Patients with Diabetic Neuropathy," Arch Phys Med Rehabil, 83, pp. 171-176 (2002).
Louis et al., "Evaluation of Normal Values for Stationary and Moving Two-Point Discrimination in the Hand," J. Hand Surg Am, 9, pp. 552-555 (1984).
Manjarrez, E et al., "Stochastic resonance in human electroencephalographic activity elicited by mechanical tactile stimuli," Neuroscience Letters, 324, pp. 213-216 (2002).
Manjarrez, E et al., "Stochastic Resonance within teh Somatosensory System: Effects of Noise on Evoked Field Potentials Elicited by Tactile Stimuli," The Journal of Neuroscience, 23, pp. 1997-2001 (2003).
Mathiowetz et al., "Adult norms for the Box and Block Test of manual dexterity," Am J. Occup Ther, 3,pp. 386-391 (1985).
McGuire, J et al., "Vibrotactile Device for Optimizing Skin Response to Vibration," UW—Milwaukee Industrial & Manufacturing Engineering, 26 pages (2009).
Merzenich, MM et al., "Progression of Change Following Median Nerve Section in the Cortical Representation of the Hand in Areas 3b and I in Adult Owl and Squirrel Monkeys," Neuroscience, 10, pp. 639-665 (1983).
Micera, S et al., "Wearable Neural Prostheses," Engineering in Medicine and Biology Magazine, 29.3, pp. 64-69 (2010).
Monzee, J et al., "The Effects of Digital Anesthesia on Force Control Using a Precision Grip," Journal of Neurophysiology, 89, pp. 672-683 (2001).
Moss, F et al., "Stochastic Resonance and Sensory Information Processing: A Tutorial and Review of Application," Clin Neurophysiol, 115, pp. 267-281 (2004).
Motawar et al., "Roles of cutaneous Sensation and Gloves with Different Coefficients of Friction on Fall Recovery During Simulated Ladder Falls," The 35th Annual Meeting of the American Society of Biomechanics (2011).
Nakayama et al., "Recovery of upper extremity function in stroke patients," the Copenhagen Stroke Study, Archives of Physical Medicine and Rehabilitation, 75, pp. 394-398, (1994).
Nathan, DE et al "Design and validation of Low-Cost Assistive Glove for Hand Assessment and Therapy During Activity of Daily Living-Focus Robotic Stroke Therapy," J Rehabil Res Dev, 46, pp. 587-602 (2009).
Parker et al., "Loss of Am Function After Stroke: Measurement, Frequency and Recovery," International Rehabilitation Medicine, 8, pp. 69-73 (1986).
Priplata, A et al., "Noise-Enhanced Human Balance Control," Phys Rev Lett, 89, pp. 238101 (2002).
Radwin, R., "Hand Anthropometry of US Army Personnel," (1991).
Roger et al., "Heart Disease and Stroke Statistics" American Heart Association, 125, pp. 2-220 (2012).
Sato, G., "Properties of the Receptor Potential in Pacinian Corpuscles," 122. pp. 610-636 (1953).
Sens, E et al., "Effects of Temporary Functional Deafferentation on the Brain, Sensation, and Behavior of Stroke Patients" J Neurosci, 32, pp. 11773-11779 (2012).
Seo, N.J et al., "Effect of Remote Sensory Noise on Hand Function Post Stroke," 8 (2014).
Tabachnick, BG et al., "Using Multivariate Statistics," 5, (2007).
Tsekos, N et al., "Magnetic Resonance-Compatible Robotic and Mechatronics Systems for Image-Guided Interventions and Rehabilitation: A Review Study," Ann Rev of Biomed. Eng., 9, pp. 351-387 (2007).
Turton et al., "Referred Sensations Following Stroke," Neurocase, 7, pp. 397-405 (2001).
Wells, W et al., "Touch Noise Increases Vibrotactile Sensitivity in Old and Young," Psychological Sci, 16, pp. 313-320 (2005).
Winstein, CJ., "Knowledge of Results and Motor Learning—Implications for Physical Therapy," Physical Therapy, 71, pp. 140-149 (1991).
Yamamoto et al., "Development of an MR-Compatible Gamma Probe for Combined MR/RI Guided Surgery," Phys. Med. Biol., 49, pp. 3379-3388 (2004).
Yekutiel, M et al., "A Controlled Trial of the Retraining of the Sensory Function of the Hand in Stroke Patients," J Neurol Neurosurg Psychiatry, 56, pp. 241-244 (1993).
Zatsiorsky, VM et al.,"Prehension Synergies," Exercise Sport Science Review, 32 (2004).
Kurita et al., "Wearable Sensorimotor Enhancer for a Fingerti based on Stochastic Resonance," specification IEEE Transactions on Human-Machine Systems, vol. 43, No. 3 (May 2013) 5 pages.
Kurita et al., "Wearable Sensorimotor Enhancer for a Fingertip based on Stochastic Resonance," specification (2011) 6 pages.
Cordo et al., "Noise in Human Muscle Spindles," scientific correspondence, Nature vol. 383, p. 769, dated Oct. 31, 1996.
Ribot-Ciscar et al, "Muscle spindle activity following muscle tendon vibration in man," Neuroscience Letters 258 (1998) pp. 147-150.

\* cited by examiner

WEARABLE DEVICE FOR IMPROVING TACTILE SENSITIVITY

CROSS-REFERENCE TO RELATED APPLICATIONS

This application claims priority to U.S. Provisional Patent Application No. 61/813,519 filed Apr. 18, 2013, the content of which is incorporated herein by reference in its entirety.

BACKGROUND

Many people in the United States experience sensory deficits after experiencing a stroke. These sensory deficits are present particularly in the hand. In fact, almost 50% of chronic stroke survivors and 85% of acute stroke survivors experience discriminatory sensory loss.

Cutaneous sensory feedback is essential for dexterity, fine finger movements, grip stability, and the setting and maintenance of force production during grip and object manipulation. For instance, tactile sensory feedback from sensory cells in the fingertips is used for motor adaptation to surface characteristics and dexterous hand movement. Tactile sensory deficit can lead to inappropriate grip force regulation and inefficient safety margins. Reduced sensory feedback may deteriorate feedback control of finger forces leading to unstable grip and object slipping against the finger, thereby hampering hand grip function.

The present application is related to improving tactile sensation.

SUMMARY

In one embodiment, the invention provides a method of increasing a tactile sensitivity of a fingertip of a user with a wearable device. The wearable device includes a vibrating element, an actuator for receiving user input, and a control circuitry. The method includes positioning the vibrating element on one of a user's arm, wrist, hand, or proximal finger segment, and activating the vibrating element to apply a vibrating force at a first magnitude. The method also includes receiving user input indicating that the user detected movement of the vibrating element at the first magnitude, and applying the vibrating force at a second magnitude to increase the tactile sensitivity of at least one fingertip of the user. The second magnitude is lower than the first magnitude.

In another embodiment the invention provides a wearable device for increasing a tactile sensitivity of a fingertip of a user. The wearable device includes a vibrating element, a securing strap for housing the vibrating element. The securing strap is configured to couple to one of a user's arm, wrist, hand, or proximal finger segment. The wearable device also includes an actuator coupled to the securing strap and configured to receive a user input and a control circuitry coupled to the vibrating element and the actuator. The control circuitry is configured to generate a vibration signal and activate the vibrating element in accordance with the vibration signal to apply a vibrating force at a first magnitude. The control circuitry is also configured to receive a user input indicating that the user detected movement of the vibrating element at the first magnitude, determine a second magnitude to apply the vibrating force, the second magnitude being lower than the first magnitude, and activate the vibrating element to apply the vibrating force at a second magnitude to increase the tactile sensitivity of at least one fingertip of the user.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
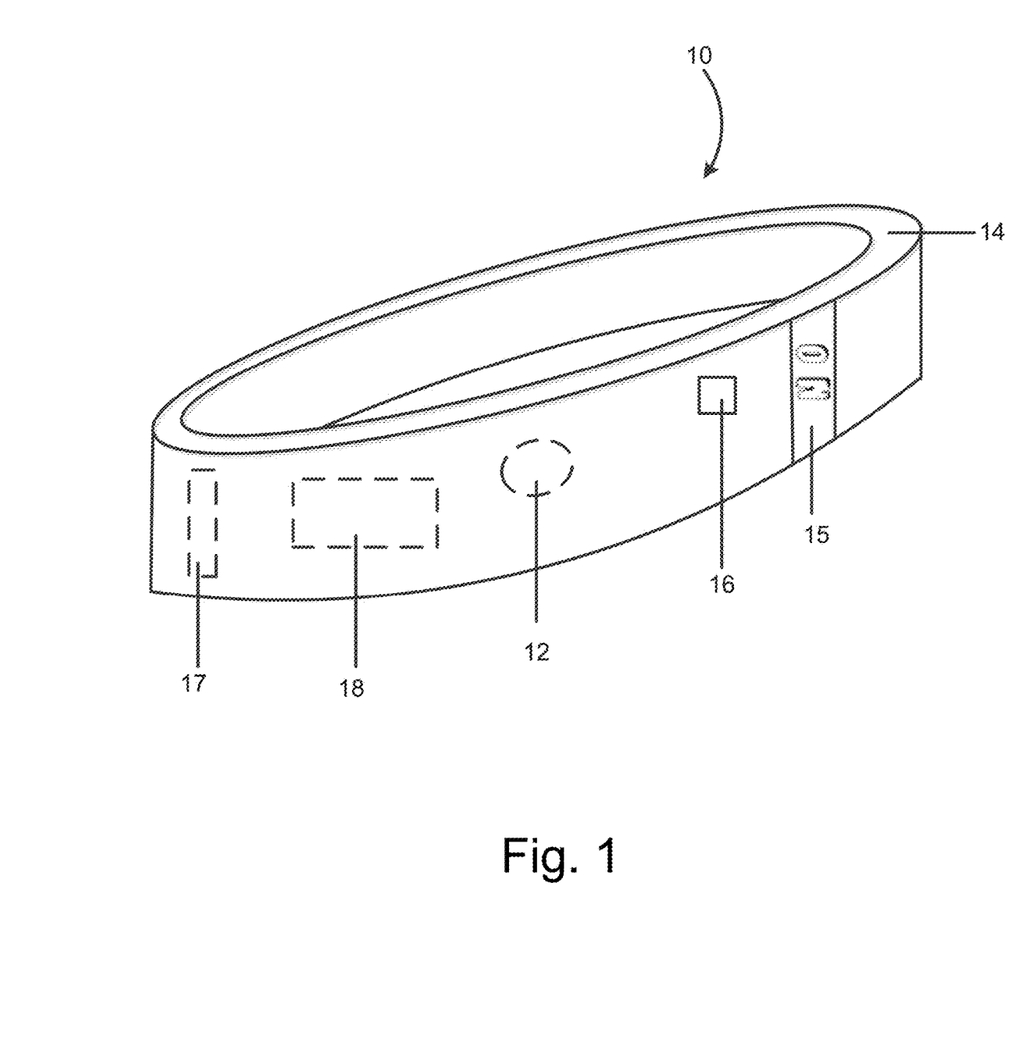
FIG. 1 is a perspective view of a wearable device.

FIG. 1 illustrates a wearable device 10 used to increase a tactile sensitivity of a fingertip of a user. In general, the wearable device 10 applies a vibrating force to an area of the hand, or proximal to the hand, of a user. The vibrating force applied on the hand or an area proximal to the hand (e.g., a hand including the palm or dorsal hand, wrist area, arm including forearm, or proximal finger segments (that is, segments other than the distal segments having the fingertips) of the user) may decrease a user's tactile sensory threshold to tactile input signals due to, for example, stochastic resonance. A user's tactile sensory threshold refers to a minimum level of vibration applied on a person's skin (e.g., on a fingertip) that a user can detect. The level of vibration may refer to a vibration force or a vibration displacement. For example, if a user has a tactile sensory threshold of approximately 2 mm for a vibrating displacement, if a vibrating element with a vibrating displacement of about 0.5 mm is placed on the user's skin, the user does not detect the vibration because the vibrating displacement (0.5 mm) is lower than the tactile sensory threshold (2 mm). If a vibrating element with a vibrating displacement of about 4 mm is placed on the user's skin, the user detects the vibration because the applied vibrating displacement (4 mm) is greater than the user's tactile sensory threshold (2 mm). The tactile sensory threshold can change from person to person, and may change according with age. It has also been documented that the sensory threshold severely increases (i.e., a greater vibration level is applied before a user can detect the vibration) when a user has experienced a stroke or a similar traumatic incident. Therefore, there has been an interest in developing devices which can decrease a user's tactile sensory threshold.

Figure 2:
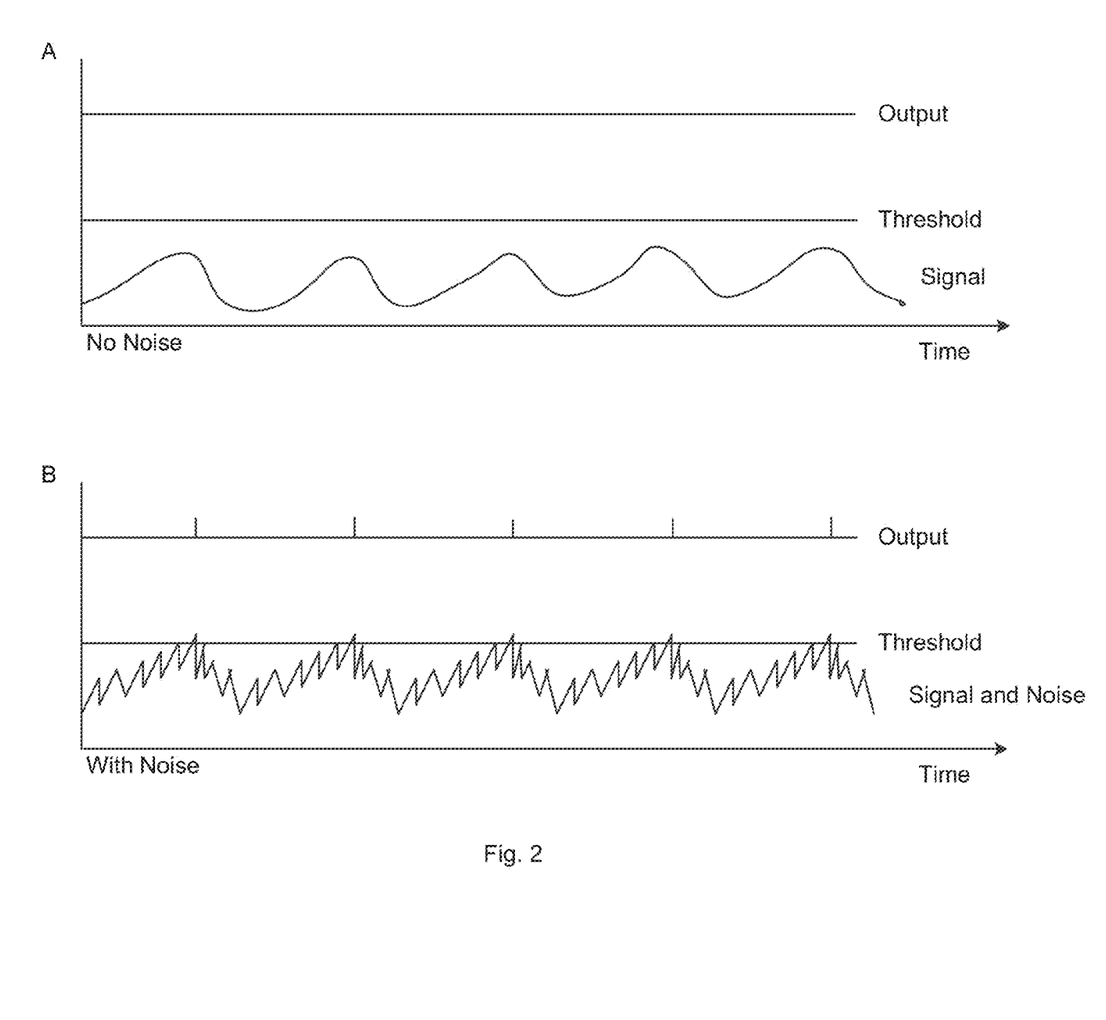
FIG. 2 is a graph of the effects of introducing noise in an input signal.

Some devices insert some type of stimulation or noise; the addition of the stimulation or noise serves to amplify the magnitude of an input sensory signal due to the phenomenon of stochastic resonance. Stochastic resonance refers to the introduction of noise in a system which facilitates the detection of weak signals. For example, as shown in FIG. 2, the addition of noise either directly into a cell (e.g., cells related to sensory systems, including peripheral or central neuronal cells, where added noise may include electrical cell stimulation) or indirectly (e.g., by stimulating the skin) increases the magnitude of the input sensory signal received by the cell. FIG. 2 shows in graph A, that without the addition of noise, the entire sensory input signal remains below the sensory threshold, and thus the cell does not detect the input signal (e.g., there's no output). However, in graph B, with the addition of noise, the sensory input signal increases slightly in magnitude, which allows the cell to detect the sensory input signal, as shown by the pulses in the output signal. It is important to note that the addition of too much noise may mask the sensory input signal. When too much noise is added to a system (e.g. if the noise is at too high of an amplitude), the sensory input signal may increase significantly in magnitude, which may cause the sensory cell to respond randomly to the sensory input signal due to the excessive amount of noise. That is, the excessive noise may cause the system to exceed the sensory threshold too often.

Some products have been developed that apply direct electrical stimulation to a sensory cell. Such products require safety precautions and high precision so that only appropriate sensory cells are electrically stimulated. Other products have been developed that apply a local vibration signal very near where a sensory input signal is received by the user. For example, a local vibration signal may be applied to a fingertip of the user to increase the tactile sensitivity of the fingertip of the user. These local vibration signals are applied very near the area expected to receive the sensory input signals because vibration signals quickly attenuate across small distances through the skin tissue. For example, vibration signals applied at a central point quickly attenuate and the amplitude of the vibration signals becomes progressively smaller for points further away from the central point. Thus, if the tactile sensitivity of the fingertip is to be increased, it was thought that local vibration signals needed to be applied very close to the fingertip to minimize the amount of signal attenuation. Therefore, it was thought that applying the vibration signal near the area to be sensitized would allow the vibration signals to actually be detected by the cell, rather than being attenuated by moving further away from the central point of the vibration.

The wearable device 10, however, applies a remote vibration signal. Rather than applying the vibration signal very near the area expected to receive the input sensory signal, the wearable device 10 applies the vibration signal at a position that is remote from the area expected to receive the input sensory signal. In some embodiments, the wearable device 10 does not rely on the vibration signal being applied physically proximate to the fingertip (or any other area where the tactile sensitivity is to be increased), but instead introduces vibrations at locations away from the fingertips which improve touch sensitivity. Without being limited by theory, the vibrations introduced by the wearable device 10 may act by remotely stimulating neural pathways associated with the fingertip, thereby sensitizing the fingertips to more readily sense tactile stimuli. The wearable device 10 then allows a user to have the fingertips free from any stimulating devices so that hands may move more freely and be able to grasp more objects without interference from any stimulating and/or wearable device.

Figure 3:
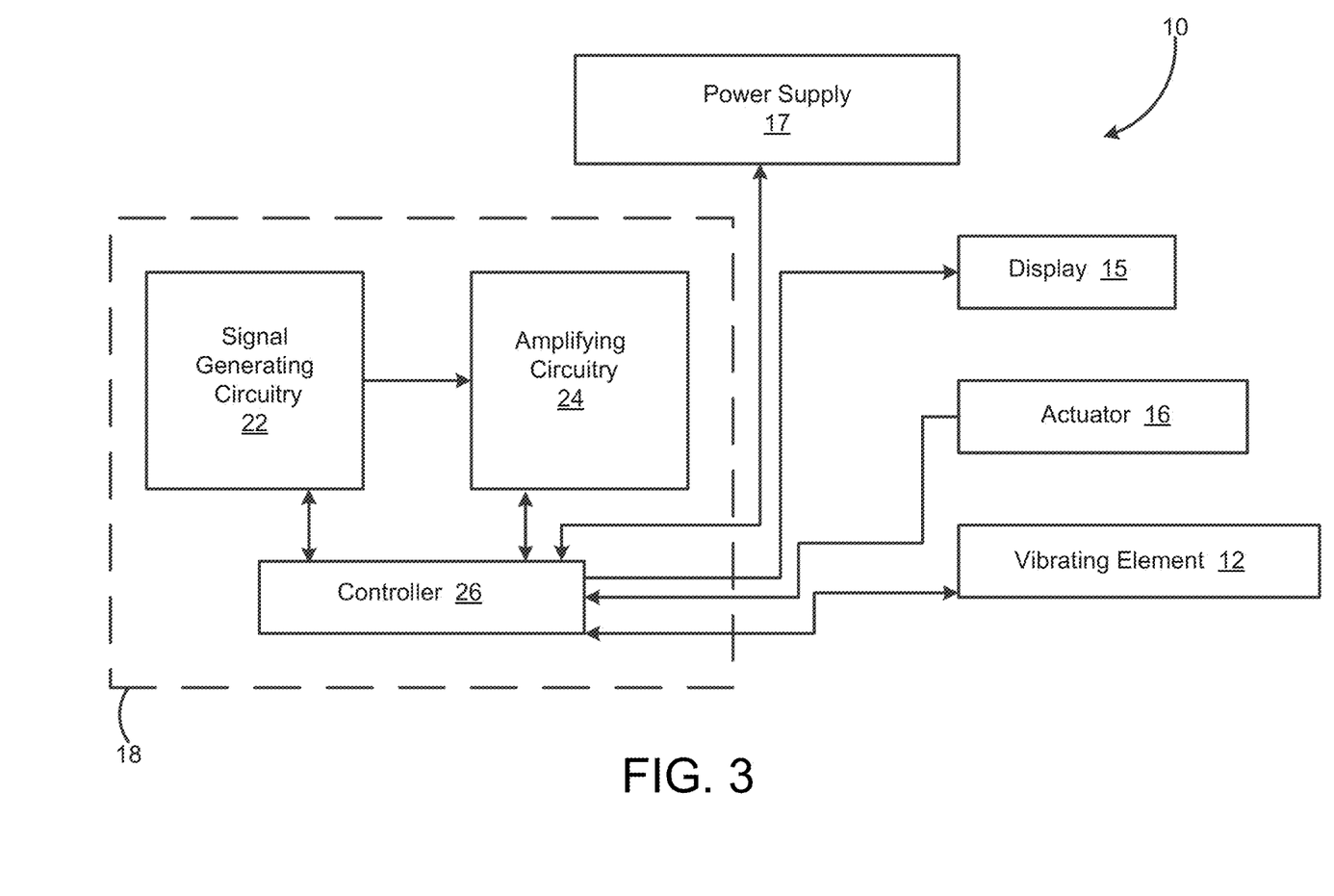
FIG. 3 is a schematic diagram of the wearable device of FIG. 1.

As shown in FIG. 3, in one embodiment the wearable device 10 includes a vibrating element 12, a securing strap 14, a display 15, an actuator 16, a power supply 17, and control circuitry 18. The power supply 17 provides power to the control circuitry 18 and to the actuator 16. In some embodiments, the power supply 17 may be a rechargeable and/or replaceable battery. The power supply 17 provides sufficient power to the control circuitry 18. In various embodiments, the power supply 17 is coupled to a power adapter circuit that modifies the voltage from the power supply 17 so that the control circuitry 18 receives power at an appropriate level. For example, the power adapter circuit may include a DC-to-DC converter or an AC-to-DC converter if the power supply 17 is an AC power source. The power adapter circuit may step down the voltage from the power supply 17 or step up the voltage from the power supply 17, based on the voltage received from the power supply 17 and the power needed by the control circuitry 18.

The securing strap 14 allows the wearable device 10 to be coupled to the user. In the some embodiments, the securing strap 14 is made from a stretchable material, such that when coupled to the user, the securing strap 14 is positioned in such a way that inhibits movement of the wearable device 10 relative to the hand of the user (e.g., a stretchable band couples tightly to the user to inhibit movement of the wearable device 10). In some embodiments, the securing strap 14 may also include a locking device, such as for example, Velcro® straps or a buckle that locks or secures the wearable device 10 in a particular position. In other embodiments, the securing strap 14 is made from an elastomeric material that conforms to the shape of a user's wrist, arm, hand, or proximal finger segments and may or may not include the locking device. In various embodiments the securing strap may be or resemble a glove, a band (e.g. a wrist band or other band which wraps around one of a user's arm, wrist, hand, or proximal fingers), or a general-purpose elastic band that can be stretched and secured in any number of positions (e.g. as an Ace™ bandage). The securing strap 14 may house the vibrating element 12 such that the position of the securing strap 14 determines the position of the vibration element 12 in relation to the user. In some embodiments, the securing strap 14 houses the vibrating element 12, the display 15, the actuator 16, the control circuitry 18, and the power supply 17. In such embodiments, all of the components of the wearable device 10 are included within a single housing (e.g., the securing strap 14). In other embodiments, the securing strap 14 houses the vibrating element 12, a first portion of the control circuitry 18, and the power supply 17, while the display 15, the actuator 16, and a second portion of the control circuitry 18 is external to the securing strap 14. In such embodiments, the display 15, the actuator 16, and the second portion of the control circuitry 18 (hereinafter collectively referred to as "the interface") may be removably coupled to the securing strap 14 and to the first portion of the control circuitry 18 to calibrate the wearable device 10 and determine operation of the vibrating element 12. For example, when a user first couples the wearable device 10 to their arm, wrist, or hand, the user may need to calibrate the wearable device 10 to determine a vibration level to be associated with the vibrating element 12. To perform such a calibration, the user may couple the external interface and perform the calibration. Once the calibration has been performed, the user may remove the interface and continue to use a smaller and lighter wearable device 10. As described above, the securing strap 14 is configured to mechanically couple the vibrating element 12 to the user's arm, wrist, hand, or proximal finger segments so that the vibrations are transmitted from the vibrating element 12 to the user's body.

The vibrating element 12 may be any electronic device that is configured to receive an electrical signal and generate movement of the vibrating element 12 based on the received electrical signal. For example, in some embodiments, the vibrating element 12 may be a piezoelectric vibrator. The piezoelectric vibrator is driven by the control circuitry 18 and oscillates (i.e., vibrates) depending on an applied voltage. In other embodiments, the vibrating element 12 may be a magnetic vibrator, a small motor with a rotational counterweight, or any device driven by an electrical signal to produce a mechanical vibration. The vibrating element 12 is mechanically coupled to a user's hand, wrist, or arm. The vibrating element 12 applies a vibrating force on the user that increases the tactile sensitivity of the user's fingertip. In one particular embodiment the vibrating element 12 is the C-3 tactor from Engineering Acoustics Inc. of Casselberry, Fla. The C-3 tactor is approximately 0.8 inches in diameter and is responsive in a range of approximately 30 Hertz to approximately 320 Hertz. The C-3 tactor has a maximal displacement in the 200-300 Hertz range, with a peak at approximately 240 Hertz. The C-3 tactor includes a central 0.3 inch diameter "contactor" element which moves, where the contactor element is surrounded by a passive housing which stabilizes the tactor against the subject's skin. Nevertheless, in various other embodiments, other devices may be used for the vibrating element 12.

In some embodiments, the wearable device 10 includes more than one vibrating element 12 and positions the vibrating elements at a plurality of locations on the arm, the wrist, or the hand such that a mechanical vibration is applied to two areas of the user. For example, a first vibrating element may be placed on a volar wrist area and a second vibrating element may be placed on a dorsal wrist area. In some embodiments, the vibration of the first vibrating element is the same as the vibration of the second vibrating element, while in other embodiments the vibration of the first vibrating element is different (may be more or less intense) than the vibration of the second vibrating element.

The actuator 16 is coupled to the control circuitry 18 and is configured to receive a user input. The actuator 16 may be a push button, a toggle button, a rotating knob, or any other button or switch configured to receive a user input. The user input may, for example, indicate when to turn on or off the wearable device 10, when the user detects a vibration, and/or when to change the vibration level of the vibrating element 12. In some embodiments, the actuator 16 is also housed in the securing strap 14 or is otherwise coupled to the securing strap 14. In other embodiments, the actuator 16 is external to the securing strap 14. In some embodiments, the wearable device 10 includes more than one actuator 16. For example, the wearable device 10 may include a power button and the input actuator 16. In some embodiments, the actuator 16 may be movable between more than two positions. For example, the actuator 16 may be movable between a first position, in which the wearable device 10 is off, a second position, in which the wearable device 10 vibrates the vibrating element 12 at a first level, a third position, in which the wearable device 10 vibrates the vibrating element 12 at a second level, and a fourth position, in which the wearable device 10 vibrates the vibrating element 12 at a third level. The first level, the second level, and the third level may each be associated with a predetermined magnitude of a vibrating force applied to vibrate the vibrating element 12. In other embodiments, however, the first level, second level, and third level may be determined by calculating a particular percentage of a reference magnitude, for example a reference magnitude that is determined during a calibration procedure and which is subject-specific, as described below.

The display 15 provides feedback to the user regarding the operation of the wearable device 10. The display 15 may include a single LED, a plurality of LEDs, an LCD screen, or any other type of display that provides feedback to the user. In the illustrated embodiment, the display 15 includes an LCD screen. The display 15 may indicate to the user that the wearable device 10 is operating. The display 15 may alternatively or additionally indicate to the user that the wearable device 10 is vibrating the vibrating element 12 at a particular level or magnitude. The display 15 may also alert the user of a condition of the wearable device 10. For example, the display 15 may display a message on the LCD screen or light the LED in a particular color to alert the user that a state of charge of the power supply 17 is below a low battery voltage, or that there is a fault within the control circuitry 18.

The control circuitry 18 is coupled to the vibrating element 12 and to the actuator 16. In some embodiments, the control circuitry 18 is also housed in the securing strap 14. In other embodiments, the control circuitry 18 is external to the securing strap 14. The control circuitry 18 includes signal-generating circuitry 22, amplifying circuitry 24, and a controller 26. The signal-generating circuitry 22 is coupled to the controller 26 and to the amplifying circuitry 24. In some embodiments, the signal-generating circuitry 22 generates a "white noise" signal used by the controller 26 to drive the vibrating element 12. As used herein, the term "white noise" refers to a signal having a substantially equal intensity at all frequencies within a given frequency range. White noise may be generated while the wearable device 10 is in use or may be prerecorded and stored, or both generated and stored white noise sources may be combined. The signal-generating circuitry 22 includes, in some embodiments, a random number generator coupled to a digital-to-analog converter in order to generate a white noise signal. In other embodiments, the signal-generating circuitry 22 includes non-transitory computer readable medium for storing a recorded portion of a white noise signal. The controller 26 may command the signal-generating circuitry 22 to generate the white noise signal. In the embodiments where the signal-generating circuitry 22 stores a recorded portion of the white noise signal, the controller 26 may command the signal-generating circuitry 22 to access the recorded white noise signal and repeatedly communicate it to the amplifying circuitry 24.

The wearable device 10 uses a white noise signal to drive and activate the vibrating element 12. Without being limited by theory, the vibrations according to the white noise signals appear to increase tactile response in the user based on the phenomenon of stochastic resonance on the input sensory signals for the tactile cells to be sensitized, for example, the tactile sensory cells in the fingertips. As noted above, a white noise signal includes a signal that has substantially the same intensity (e.g., power) at each frequency for a given frequency bandwidth. For example, for a tactile sensory cell, the active frequency bandwidth (i.e., the frequency of signals detected by a tactile sensory cell) includes frequencies from zero Hertz to 500 Hertz. Thus, a white noise signal within that frequency range includes a signal with approximately equal intensities at each frequency for frequencies between zero Hertz to 500 Hertz. A narrower range for the active bandwidth of the tactile sensory cells in some embodiments is 30 Hertz to 300 Hertz. Thus, in some embodiments the signal-generating circuitry 22 generates a white noise signal with a frequency bandwidth of 30 Hertz to 300 Hertz. The frequency bandwidth of the white noise signal may change based on particular sensory cells being sensitized. For example, different sensory cells detect (e.g., generate an action potential) sensory input signals at different frequencies. A Pacinian corpuscle detects sensory input signals with a frequency of about 300 Hertz, so a frequency bandwidth between 200 Hertz and 400 Hertz may be effective, while a Meissner corpuscle detects sensory input signals with a frequency of around 50 Hertz, so a frequency bandwidth between 0 Hertz and 100 Hertz may be effective. Similarly, Ruffini corpuscles and Merkel discs may detect sensory input signals with different frequencies and the frequency bandwidth for the white noise signal may be adjusted according to which sensory cells are sensitized. In some embodiments, the wearable device 10 may be configurable by a user to provide vibrations at one or more of the above-noted ranges to increase sensitivity of a particular sensory cell. For example, a user may choose between applying vibrations between 200-400 Hertz to specifically increase sensitivity of the Pacinian corpuscles.

Additionally, the frequency bandwidth of the white noise signal may be adjusted based on the frequency of generated action potentials in a neuron. Physiologically, action frequencies of up to 200-300 Hertz are routinely observed, so a white noise signal with a frequency bandwidth of 0-400 Hertz may also be applied to sensitize the sensory signals. The maximum action potential frequency is 500-1000 Hertz; thus, a wider frequency bandwidth of 0-1000 Hertz may also be used for the white noise signal.

In various embodiments, a white noise signal may allow for the various tactile input signals received by the tactile sensory cells to be equally amplified. That is, any tactile input within the given frequency range (e.g. 30-300 Hertz) may stand an equally likely chance of being detected. On the other hand, if the vibrating element 12 were instead driven by a signal which includes only one or a small range of frequencies then only external tactile stimuli at those frequencies would be subject to the decreased sensory threshold resulting from use of the wearable device 10. Similarly, by using a white noise signal, neurons that produce action potentials at different frequencies may also have an equally likely chance of being stimulated and thus subject to the decreased sensory threshold resulting from use of the wearable device 10. In contrast, if a signal including only one or a small range of frequencies is used, and then it may be possible for only some of the neurons firing action potentials at those frequencies would be subject to the decreased sensory threshold resulting from use of the wearable device 10.

The amplifying circuitry 24 is coupled to the signal-generating circuitry 22, the controller 26, and the power supply 17. The amplifying circuitry 24 receives the white noise signal generated by the signal-generating circuitry 22 and amplifies that signal to a predetermined level. The amplifying circuitry 24 receives a signal from the controller 26 that determines the level of amplification for the signal. In some embodiments, the amplifying circuitry 24 includes an operational amplifier circuit having a potentiometer. The controller 26 then changes the resistance of the potentiometer to change the level of amplification of the white noise signal.

The controller 26 is coupled to the signal-generating circuit 22, the amplifying circuitry 24, the actuator 16, and the power supply 17. The controller 26 receives a user input through the actuator 16. For example, the controller 26 may determine that the wearable device 10 has just been turned on by a user through a power button or through the actuator 16. In some embodiments, the controller 26 stores in memory (e.g., in a non-transitory computer readable medium) a vibration level with which to activate the vibrating element 12. The vibration level may be based on a typical range for a person's sensory threshold and a typically effective noise level (e.g., fraction of sensory threshold). The typical range for a person's sensory threshold may be determined by accumulating data and observing typical ranges. Similarly, the effective noise level may also be determined by trials. For example, from testing and trials, it may be determined that 70% of the people have a sensory threshold of about 3 mm for a vibrating displacement and that the effective noise range is from about 30% to 75% of the sensory threshold (i.e., 0.9 mm-2.1 mm). Thus, the controller 26 may store a vibration level of 1.5 mm to activate the vibrating element 12. The stored vibration level is then expected to increase sensitivity for approximately 70% of people. In such embodiments, the controller 26 receives a user input through the actuator 16 to turn on and turn off the device and then automatically activates the vibrating element 12 at the stored vibration level.

In other embodiments, the controller 26 is configured to determine a user's tactile sensory threshold automatically upon turning on the wearable device 10. To determine a user's tactile sensory threshold, the controller 26 is configured to vibrate the vibrating element 12 at different magnitudes to determine the lowest magnitude for which the user indicates through the actuator 16 that the user detected movement of the vibrating element 12.

Figure 4:
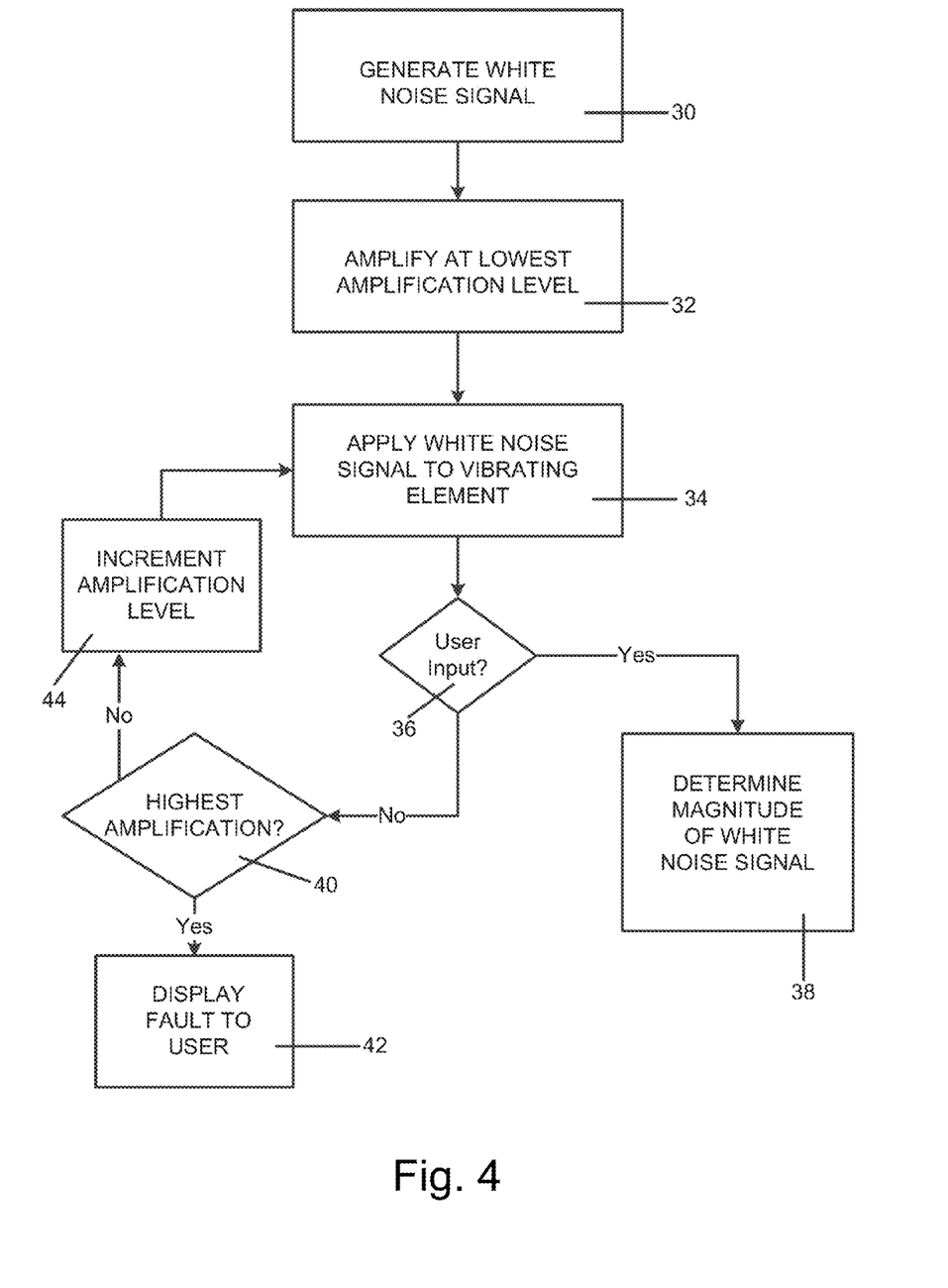
FIG. 4 is a flowchart showing a method of determining a user's tactile sensory threshold.

FIG. 4 illustrates a first method for determining the user's tactile sensory threshold. The controller 26 sends a signal to the signal-generating circuitry 22 to generate the white noise signal (block 30). The controller 26 also sends a signal to the amplifying circuitry 24 to amplify the white noise signal at the lowest level of amplification (block 32) to produce the low white noise signal. In some embodiments, this may mean that the amplifying circuitry 24 does not amplify the white noise signal, i.e. if the lowest level of amplification is zero. The low white noise signal is then applied to the vibrating element 12 to vibrate the vibrating element 12 at the current amplification level (block 34). The controller 26 then checks whether the actuator 16 indicates that a user input has been received indicating that the user has detected the movement of the vibrating element 12 (block 36). If the controller 26 receives the user input through the actuator 16, the controller 26 determines the magnitude that was associated with the white noise signal when the controller 26 received the user input (block 38), which is taken as the lowest user-detectable signal magnitude. The lowest magnitude of the white noise signal when the user detects movement of the vibrating element 12 corresponds to the tactile sensory threshold for the user.

If the controller 26 does not receive user input from the actuator 16, the controller 26 then checks if the amplification level is the highest amplification from the amplifying circuitry 24 (block 40). If the controller 26 determines that the amplification level is at the highest level the controller 26 determines a fault in the control circuitry 18 and alerts the user of the fault (block 42). If the controller 26 determines that the amplification level is not at the highest level of amplification, the controller 26 commands the amplifying circuitry 24 to increase the amplification level by one unit (block 44). The unit for increasing the amplification level may be determined, for example, by the potentiometer used in an operational amplifier circuit. Alternatively, the unit of amplification may be determined in a digital manner using, for example, a digital counter. The increments may be determined, for example, as a percentage of the maximum amplification (e.g. a maximum voltage level); the percentages may be in increments of 1%, 5%, 10%, or other suitable percentages of a maximum level. Once the amplification has been increased and applied to the vibrating element 12 (block 34), the controller 26 checks again for a user input from the actuator 16 (block 36). Thus, the controller 26 continues to increase the amplification level for the white noise signal until the user detects movement of the vibrating element 12 and signals this detection through the actuator 16, at which point the controller 26 determines the tactile sensory threshold for the user.

In some embodiments, the controller 26 may increase the amplification level linearly by more than one unit, for example by ten units, until the user indicates, via the actuator 16, that the user detects movement of the vibrating element 12. Once the user input is received from the actuator 16, the controller 26 applies the last amplification level not detected by the user and begins to increase the amplification level by one unit at a time to accurately determine the user's tactile sensory threshold.

Figure 5:
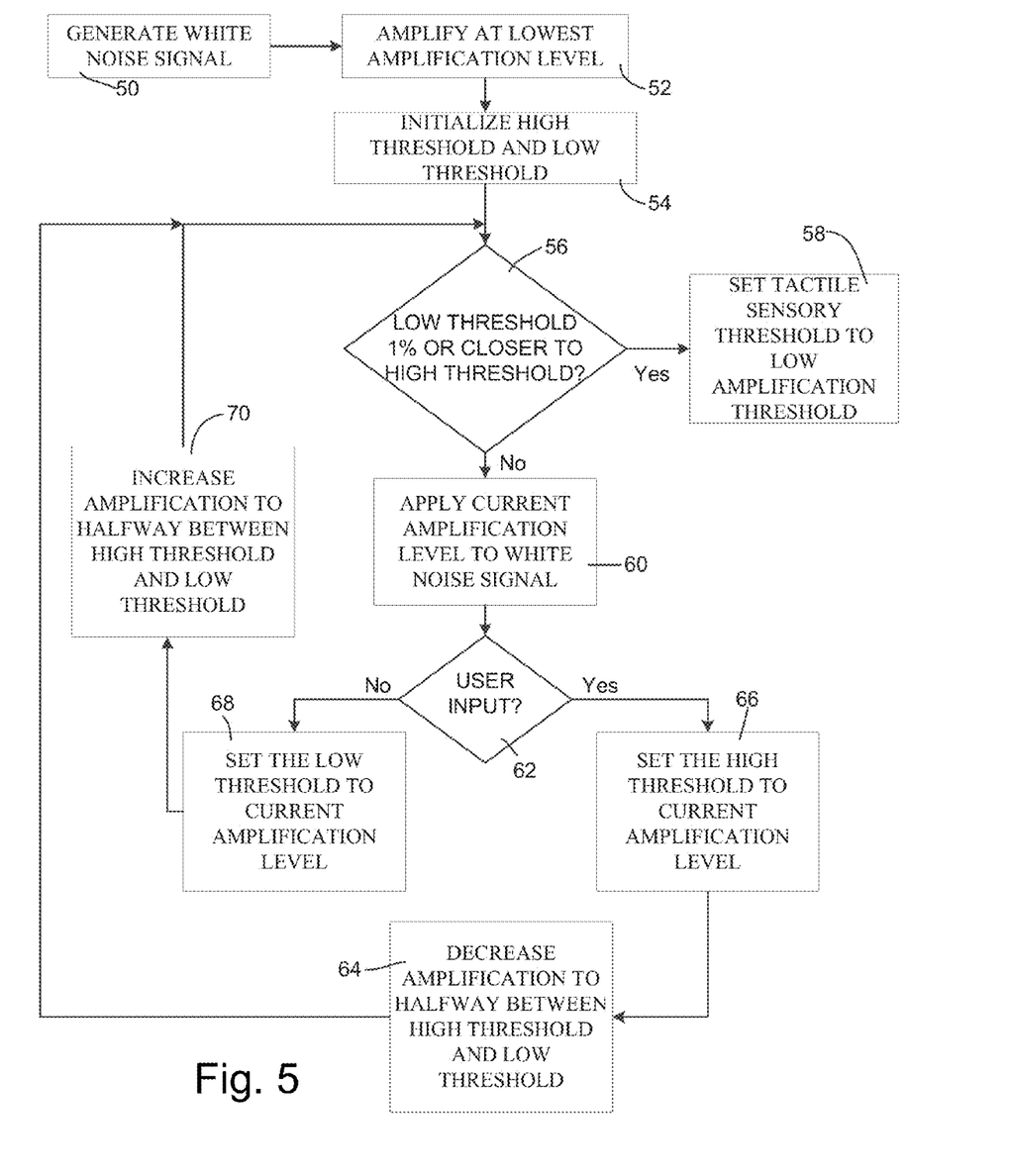
FIG. 5 is a flowchart showing a second method of determining a user's tactile sensory threshold.

FIG. 5 illustrates a second method for determining the user's tactile sensory threshold. First, the controller 26 sends a signal to the signal-generating circuitry 22 to generate the white noise signal (block 50). The controller 26 also sends a signal to the amplifying circuitry 24 to amplify the white noise signal at the lowest level of amplification (block 52) to produce the low white noise signal. In some embodiments, this may mean that the amplifying circuitry 24 does not amplify the white noise signals, i.e., if the lowest level of amplification is zero. Then, the controller 26 initializes a low amplification threshold at the lowest amplification level, for example, zero percent of amplification and initializes a high amplification threshold at the highest amplification level, for example, 100 percent of amplification (block 54). The controller 26 then determines if the low amplification threshold is 1% or closer to the high amplification threshold (block 56). When the low amplification threshold is 1% or closer to the high amplification threshold, the controller 26 determines the magnitude that was associated with the white noise signal when the controller 26 applied the low amplification level (block 58), which is considered to be the lowest user-detectable signal magnitude. The lowest magnitude of the white noise signal when the user detects movement of the vibrating element 12 corresponds to the tactile sensory threshold for the user.

If the low amplification threshold is more than 1% lower than the high amplification threshold, the controller 26 applies the white noise signal at the current amplification level to the vibrating element 12 to vibrate the vibrating element 12 (block 60). The controller 26 then checks whether the actuator 16 indicates that a user input has been received indicating that the user has detected the movement of the vibrating element 12 (block 62). If the controller 26 receives the user input through the actuator 16, the controller 26 sets the high amplification threshold to the current level of amplification (block 64). The controller then decreases the amplification level to a new amplification level halfway between the low amplification threshold and the high amplification threshold (block 66). Once the new amplification level is determined, the controller 26 checks again if the low amplification threshold is 1% or closer to the high amplification level (block 56).

Referring back to block 62, if the controller 26 does not receive user input from the actuator 16, the controller 26 then sets the low amplification threshold to the current level of amplification (block 68). The controller 26 then increases the amplification level to a new amplification level halfway between the low amplification threshold and the high amplification threshold (block 70). Once the new amplification level is determined, the controller 26 checks again if the low amplification threshold is 1% or closer to the high amplification level (block 56). The controller 26 continues to increase and decrease the amplification level until the low amplification threshold is 1% or closer to the high amplification threshold. Determining the tactile sensory threshold in this manner may result in a faster determination of the user's tactile sensory threshold since not all of the amplification levels are tried. By increasing/decreasing the amplification levels to a new amplification level halfway between the low amplification threshold and the high amplification threshold, the controller 26 is able to quickly dismiss amplification levels that are far away from the user's tactile sensory threshold and more closely monitor the amplification levels closer to the user's tactile sensory threshold.

For example, to illustrate an example of the process of the method of FIG. 5, the low amplification threshold is first set to zero percent of amplification (i.e., no amplification) and the high amplification threshold is first set to 100 percent of amplification (i.e., the highest level of amplification). Then the lowest level of amplification is applied to the white noise signal, likely resulting in no detected movement by the user. The amplification level is increased to a new amplification level halfway between 0% (i.e., the low amplification threshold) and 100% (i.e., the high amplification threshold). The new amplification level of 50% is then applied to the white noise signal, likely resulting in a detected movement by the user. The amplification level is then decreased to a new amplification level (25%) halfway between 0% (i.e., the low amplification threshold) and 50% (i.e., the high amplification threshold). The new amplification level of 25% is then applied to the white noise signal, likely resulting in a detected movement by the user. The amplification level is then again decreased to a new amplification level (12%) halfway between 0% (i.e., the low amplification threshold) and 25% (i.e., the high amplification threshold). The new amplification level of 12% is then applied to the white noise signal, resulting in no detected movement by the user. The amplification level is then increased to a new amplification level (19%) halfway between 12% (i.e., the low amplification threshold) and 25% (i.e., the high amplification threshold). The new amplification level of 19% is then applied to the white noise signal, resulting in a detected movement by the user. The amplification level is then decreased to a new amplification level (16%) halfway between the low amplification threshold (12%) and the high amplification threshold (19%). The new amplification level is applied to the white noise signal, resulting in no detection of movement by the user. The amplification level is then increased to a new amplification level (18%) halfway between the low amplification threshold (16%) and the high amplification threshold (19%). The new amplification level is then applied to the white noise signal, resulting in no detection of movement by the user. The amplification threshold is then increased to a new amplification level (18.5%) halfway between the low amplification threshold (18%) and the high amplification threshold (19%). However, the low amplification threshold (18%) is within 1% of the high amplification threshold (19%). Thus, the controller 26 determines the magnitude of the white noise signal at the low amplification threshold to determine the user's tactile sensory threshold. In some embodiments, the control circuitry 18 also includes an attenuator that attenuates the white noise signal. In such embodiments and when employing the method illustrated in FIG. 5, the controller 26 may switch between amplifying the white noise signal and attenuating the white noise signal at different levels to obtain an accurate determination of the user's tactile sensory threshold.

The tactile sensory threshold may vary based on a number of factors, such as the individual user, the exact position of the vibrating element on the user's arm/wrist/palm, and other factors. In addition, the palm may also include the proximal portions of the fingers, so that a suitably-adapted version of the wearable device 10 may be secured to one or more of the proximal segments of a user's fingers and thereby increase tactile sensitivity of one or more of the user's fingertips on that hand. In some embodiments, the remote vibration applied by the wearable device 10 also increases tactile sensitivity of different areas of the hand, for example, tactile sensitivity on the palm may also increase. Determining the tactile sensory threshold for the user upon powering of the wearable device 10 compensates for the variation of the tactile sensory threshold. By determining a user's tactile sensory threshold before each use of the wearable device 10, the controller 26 takes into account the exact position of the vibrating element 12 as well as the specific user. In some embodiments, the tactile sensory threshold of a user may also vary with age and time, determining the tactile threshold before each use of the wearable device 10 also compensates for changes in the tactile sensory threshold due to time.

Once the controller 26 has determined the tactile sensory threshold for the user, the controller 26 commands the amplifying circuitry 24 to amplify the white noise signal at a second magnitude. In some embodiments the second magnitude is based on a predetermined percentage of a first magnitude (i.e., the tactile sensory threshold for the user). In other embodiments, the controller 26 receives user input through the actuator 16 or through a different actuator that indicates the predetermined percentage that should be used to calculate the second magnitude. For example, the user input may indicate one of a first level, a second level, and a third level. Each level may be associated with a particular predetermined percentage. For example, the first level may be associated with 40% of the tactile sensory threshold, the second level may be associated with 60% of the tactile sensory threshold, and the third level may be associated with 80% of the tactile sensory threshold; nevertheless other percentages may be used for each level. The controller 26 determines the percentage based on the user input and calculates the second magnitude accordingly. The controller 26 then commands the amplifying circuitry 24 to amplify the white noise signal at the second magnitude, and the white noise signal is then used to drive the vibrating element 12 such that the vibrating element 12 vibrates at the specified percentage of the tactile sensory threshold value. In general, the second level is selected so that when the vibrating element 12 is driven by white noise that is amplified at the second level, the user does not perceive the vibrations, i.e. the vibrations are sub-threshold.

In other embodiments, the controller 26 automatically calculates the second magnitude based on a stored percentage, for example 60% of the tactile sensory threshold. The controller 26 then commands the amplifying circuitry 24 to amplify the white noise signal at the second magnitude, and the white noise signal is then used to drive the vibrating element 12 such that the vibrating element 12 vibrates at only 60%, for example, of the tactile sensory threshold. In some embodiments, the controller 26 includes the functionality of the signal-generating circuitry 22 and the amplifying circuitry 24, for example, if the controller 26 is a microprocessor including signal-generating capabilities and amplifying capabilities. In such embodiments, the controller 26 does not command the signal-generating circuitry 22 and/or the amplifying circuitry 24, but instead is configured to perform the functionality of the signal-generating circuitry 22 and the amplifying circuitry 24. In such embodiments, the controller 26 may include non-transitory computer readable medium to store instructions executable by the microprocessor. The non-transitory computer readable medium may also store the white noise signal and the percentage (or percentages) to calculate the second magnitude.

By applying a sub-threshold vibratory stimulation through the vibrating element 12, the wearable device 10 increases the tactile sensitivity of a user's fingertips. Without being limited as to theory, it is believed that the tactile sensitivity of the user's fingertips increases because the sub-threshold vibratory stimulation in an area remote from the user's fingertips excites neural pathways including the sensory neural pathways associated with the user's fingertips. By exciting the sensory neural pathway associated with the user's fingertips, the sensory input signal may not need to be as strong to be detected by the tactile sensory cells of the user's fingertips. Without being limited as to theory, the remote sub-threshold vibratory stimulation may excite the brain, including, for example, the thalamus, parietal lobe, or other parts of the brain relating to somatosensation and resulting motor control such as somatosensory cortical portions of the brain. By exciting the somatosensory cortical portion of the brain associated with the arm, wrist, and hand, the increased brain activity may strengthen sensory feedback, increase sensorimotor information processing and integration to the hand area, for example by "priming" particular sensory regions so that they are more receptive to subsequent tactile inputs. Since the brain increases activity in the somatosensory portion of the brain, the brain activity may cause the sensory cells to become more receptive to sensory input signals, thereby lowering a user's tactile sensory threshold. Accordingly, for example, the sensory pathway may include receiving the sub-threshold vibration on a wrist area. The somatosensory cortex may then detect the subsensory signal and increase sensory and motor signal integration in the brain, which causes increases sensory and motor functions of the hand, particularly the fingertips. Alternatively, it may be that a weak signal may be detected by a few tactile sensory cells, but may not be strong enough to excite the neurons in the brain that result in the person's perception in the signal. By exciting a sensory neural pathway, the neurons in the brain that result in perception of the tactile input signal may become capable of detecting weaker signals. Additionally, since the sub-threshold vibratory stimulation is applied remotely from the user's fingertips, more than one fingertip may experience increased tactile sensitivity. Thus, only one wearable device 10 may be needed to increase the tactile sensitivity of more than one of the user's fingertips in one hand. Nevertheless, other mechanisms instead of, or in addition to, the excitation of neural pathways may be responsible for the increase in tactile sensitivity that is observed when sub-threshold vibratory stimuli are applied.

Figure 6:
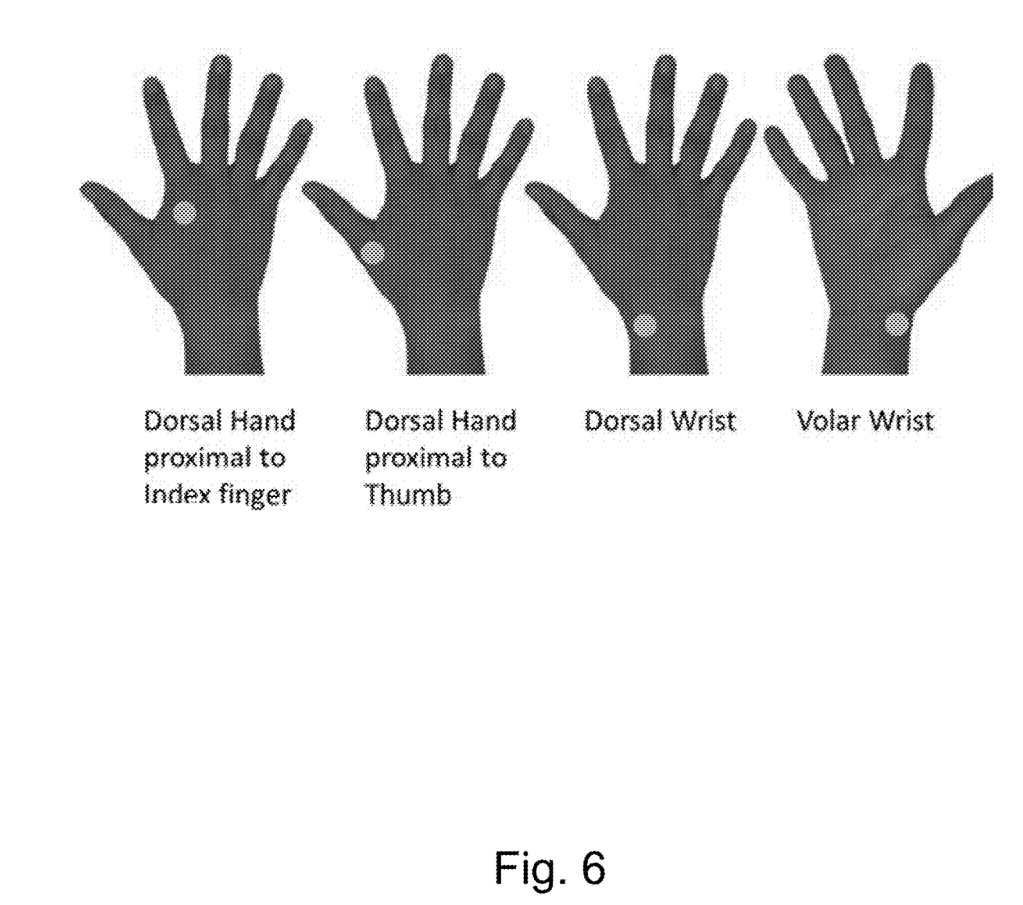
FIG. 6 shows positions for which the vibrating element of the wearable device of FIG. 1 was tested.

The vibrating element 12 of the wearable device 10 was tested using a monofilament test, as is known to those skilled in the art. The monofilament test includes touching a user's fingertip with a nylon monofilament to detect any subjective absence of touch perception. The monofilament test using vibrating element 12 was performed under different conditions. First, the vibrating element 12 was positioned at four distinct locations of the hand and wrist, as shown in FIG. 6.

Figure 6A:
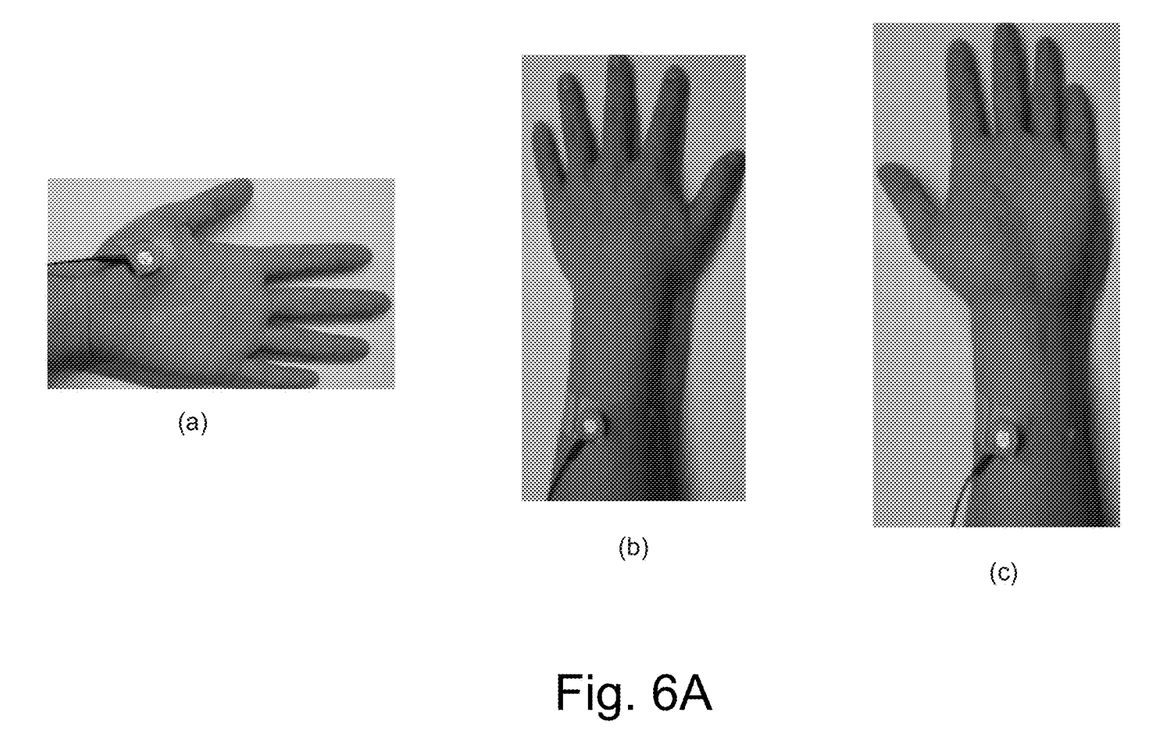
FIG. 6A shows additional positions for which the vibrating element of the wearable device of FIG. 1 was tested.

The four locations include (1) a dorsal portion of a user's hand proximate the user's index finger, (2) the dorsal portion of the user's hand proximate the user's thumb, (3) a dorsal portion of the user's wrist, and (4) a volar portion of the user's wrist. At each of the four locations, sub-threshold vibratory stimulation was provided at three different levels: at 40% of the tactile sensory threshold, 60% of the tactile sensory threshold, and at 80% of the tactile sensory threshold. The monofilament test results showed that stimulating any of the four locations of the hand and wrist, at any of the tested levels, increases tactile sensitivity of at least the index fingertip and the tip of the thumb. In other embodiments, the tactile sensitivity of all the user's fingertips may be increased. Thus, the wearable device 10 may be configured to remotely apply a vibratory stimulation to a user to increase the tactile sensitivity of the user's fingertip. In other embodiments, the vibrating element 12 of the wearable device 10 was also tested, by using surface electromyography (EMG) on upper limb muscles, when the vibrating element 12 was positioned at the three distinct locations of the palm and the arm, as shown in FIG. 6A. The three locations include (a) a thenar eminence (a palm portion of a user's hand proximate the user's thumb), (b) a dorsal forearm portion, and (c) a volar forearm portion.

Figure 7:
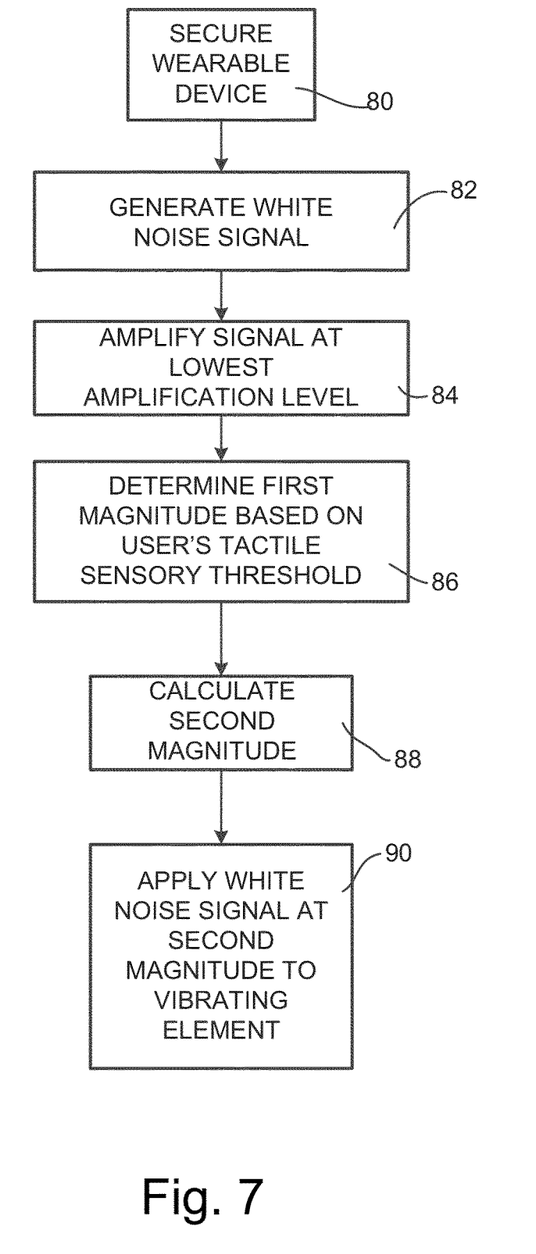
FIG. 7 is a flowchart showing the operation of the wearable device of FIG. 1.

FIG. 7 illustrates operation of the wearable device 10 to increase tactile sensitivity in a user's fingertips. First, the wearable device 10 is secured to a user and the vibrating element 12 is positioned on the wrist, the hand, or the arm of the user (block 80). The wearable device 10 then generates a white noise signal (block 82). The white noise signal is then amplified at the lowest level such that a white noise signal with a magnitude of approximately zero is outputted (block 84). Then, a first magnitude of the vibrating signal is determined based on the user's tactile sensory threshold (block 86). The user's tactile sensory threshold may be determined by a first method as shown in FIG. 6, a second method as shown in FIG. 5, or by a different method (e.g., the user's tactile sensory threshold may be stored in the control circuitry 18). In some embodiments, the first magnitude corresponds to the user's tactile sensory threshold, while in other embodiments the first magnitude is slightly lower than the user's tactile sensory threshold. Then the wearable device 10 calculates a second magnitude which is lower than the first magnitude (block 88). As explained above, in some embodiments, the second magnitude is calculated based on a stored predetermined percentage of the first magnitude, and in other embodiments, the second magnitude is calculated based on a user input. Then, the wearable device 10 applies the white noise signal at the second magnitude such that the vibrating element 12 is vibrated at the second magnitude (block 90), thereby increasing the tactile sensitivity of the user's fingertips.

In addition to decreasing the tactile sensory threshold (and thereby increasing touch sensitivity) for users who have aged, had strokes, or other trauma, the disclosed invention can also be used to lower the tactile sensory threshold for users in particular situations or occupations. For example, users that require high-precision manual dexterity could benefit from the disclosed invention, including surgeons, laboratory and manufacturing personnel, and product and other designers (e.g. to inspect textured materials).

In various embodiments the user may experience increased tactile sensitivity in not only one or more fingertips but also in other regions of the hand or forearm. In still other embodiments the wearable device 10 may be adapted for use on other parts of the body, for example the ankle, in order to increase tactile sensitivity in other parts of the body, for example the foot including the toes.

Thus, the invention provides, among other things, a wearable device configured to apply a remote vibratory stimulation to thereby increase tactile sensitivity in a user's fingertips. Various features and advantages of the invention are set forth in the following claims.

What is claimed is:

1. A method for enhancing sensory feedback of a target location on a subject comprising:
   positioning a vibrating element at a first location of the subject, wherein the first location is separated from the target location by a first distance, wherein the first location and the target location are positioned on a same limb of the subject, and wherein the first location is selected from a group consisting of a dorsal wrist area, a volar wrist area, a volar forearm portion, a dorsal forearm portion, and a thenar eminence area, and wherein the target location includes a fingertip of the subject;
   activating the vibrating element to apply a vibrating force at a first magnitude, wherein the first magnitude provides the lowest detectable vibrating force for the subject;
   adjusting the vibrating force to a second magnitude, the second magnitude being less than 100% of the first magnitude;
   applying the vibrating force at the second magnitude; and
   increasing sensitivity at the target location in response to the vibrating force at the second magnitude applied at the first location.

2. The method of claim 1, wherein the vibrating element is incorporated into a device further comprising an actuator for receiving input from the subject and a control circuitry, wherein the control circuitry is coupled to the actuator and the vibrating element, and wherein the control circuitry relays input from the actuator to the vibrating element, wherein the step of activating the vibrating element is performed by the subject activating the actuator thereby signaling the control circuitry to generate a white noise signal such that the vibrating element vibrates in accordance with the white noise signal.

3. The method of claim 2, wherein the white noise signal includes a signal with a substantially equal intensity at each frequency between the frequencies of zero Hertz and 500 Hertz.

4. The method of claim 2, wherein the white noise signal includes a signal with a substantially equal intensity at each frequency between the frequencies of 30 Hertz to 300 Hertz.

5. The method of claim 1, wherein the step of activating the vibrating element includes applying the vibrating force initially at a magnitude of approximately zero and increasing the vibrating force until the first magnitude is achieved.

6. The method of claim 5 further comprising the step of the subject applying an input to an actuator to indicate the first magnitude.

7. The method of claim 1, wherein the step of activating the vibrating element to apply the vibrating force at the first magnitude includes the following steps:
   (a) applying an initial vibrating force at an initial magnitude;
   (b) applying a second vibrating force that possesses a lower magnitude than the initial vibrating force and is undetectable by the subject;
   (c) continuing to apply vibrating forces at incrementally lower magnitudes than that associated with the initial vibrating force, wherein between each incrementally lower magnitude, a vibrating force is applied at an incrementally higher magnitude than that associated with the second vibrating force; and (d) continuing with step (c) until the first magnitude is achieved.

8. The method of claim 1, wherein the second magnitude is from about eighty percent of the first magnitude to about forty percent of the first magnitude.

9. The method of claim 1, wherein upon applying the vibrating force at the second magnitude, the subject experiences improved grip strength or reduced reaction time.

10. The method of claim 1, wherein the first location is the dorsal or volar wrist area.

11. The method of claim 1, wherein the step of adjusting the vibrating force to a second magnitude is performed by the following step:

activating an actuator coupled to the vibrating element through a control circuitry, wherein the control circuitry adjusts the vibrating force to the second magnitude according to a predetermined percentage associated with a desired level indicated by the subject, and wherein the predetermined percentage is from about eighty percent of the first magnitude to about forty percent of the first magnitude.

12. The method of claim 1 further comprising the step of determining the second magnitude based on one or more of the group selected from the first distance, the target location, and the subject's sensory threshold for detecting the vibrating force.

13. The method of claim 1 wherein the sensory feedback is cutaneous sensory feedback.

14. A system for enhancing sensory feedback of a target location on a user, the system comprising:

a vibrating element in a housing, wherein the housing is sufficient to secure the vibrating element at a first location selected from the group consisting of a dorsal wrist area, a volar wrist area, a volar forearm portion, a dorsal forearm portion, and a thenar eminence area, wherein the first location is separated by a distance from the target location, wherein the first location and the target location are positioned on a same limb of the user, and wherein the housing is sufficient to position the vibrating element in a manner to apply a vibrating force to the first location of the user, and wherein the target location includes a fingertip of the user;

a controller configured to receive input from the user; and a control circuitry coupled to the vibrating element and the controller, the control circuitry configured to generate a vibration signal based on input received by the controller, wherein the vibration signal informs the vibratory force to be applied to the vibratory element, wherein the vibratory force includes at least a first magnitude and a second magnitude, wherein the first magnitude provides the lowest detectable vibrating force for the subject, and wherein the second magnitude is less than 100% of the first magnitude, and wherein the vibratory force at the second magnitude applied at the first location increases sensitivity at the target location.

15. The system of claim 14, wherein the vibration signal comprises a white noise signal, and wherein the control circuitry is configured to generate the white noise signal using a random number generator and a digital-to-analog converter.

16. The system of claim 14, wherein the vibration signal comprises a white noise signal, and wherein the control circuitry is configured to store a recorded portion of a white noise signal and generate the white noise signal based on the recorded portion of the white noise signal.

17. The system of claim 14, wherein the control circuitry is configured to calculate the second magnitude based on a predetermined percentage of the first magnitude, wherein the predetermined percentage is not greater than eighty percent.

18. The system of claim 14, wherein the vibration signal comprises a white noise signal, and wherein the white noise signal includes a signal having an approximately equal intensity at each frequency for frequencies between 30 Hertz and 300 Hertz.

19. The system of claim 14, wherein the housing is a securing strap configured to couple the vibrating element to the first location.

20. The system of claim 19 wherein the enhanced sensory feedback improves grip strength or reduces reaction time of the user.

21. A method for enhancing sensory feedback of a target location on a subject comprising:

positioning a vibrating element at a first location of a first limb of the subject, the first location being one selected from a group consisting of a dorsal wrist area, a volar wrist area, a volar forearm portion, a dorsal forearm portion, and a thenar eminence area, and wherein the target location includes a fingertip of the first limb of the subject;

activating the vibrating element to apply a vibrating force at a magnitude, wherein the magnitude provides a vibrating force that is smaller than the lowest detectable vibrating force for the subject; and improving function at the target location in response to the vibrating force at the magnitude applied at the first location.

* * * * *